US00PP16113P3

(12) United States Plant Patent
Crawford

(10) Patent No.: US PP16,113 P3
(45) Date of Patent: Nov. 15, 2005

(54) ***LIGULARIA* PLANT NAMED 'BRITT-MARIE CRAWFORD'**

(50) Latin Name: *Ligularia dentata*
Varietal Denomination: Britt-Marie Crawford

(76) Inventor: James Crawford, Naughton House, Wormit, Fife, Scotland (GB), DD6 8RN ( * ) Notice: Subject to any disclaimer, the term of this patent is extended or adjusted under 35 U.S.C. 154(b) by 336 days.

(21) Appl. No.: 10/294,295

(22) Filed: Nov. 14, 2002

(65) Prior Publication Data

US 2004/0098776 P1 May 20, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Miller, Johnson, Snell & Cummiskey, P.L.C.

(57) ABSTRACT

*Ligularia dentata* 'Britt-Marie Crawford' is a new and distinct cultivar of Ragwort with very dark purple brown foliage that remains effective throughout the growing season, and effective as a potted plant or landscape specimen or mass for the bold foliage effect and colorful yellow-orange glower display.

2 Drawing Sheets

BACKGROUND OF THE PLANT

The present invention relates to the new and distinct Ragwort plant, botanically known as *Ligularia dentata* (A. Gray), and hereinafter referred to by the cultivar name 'Britt-Marie Crawford'. The stated cultivar is valued for its unique, deep, dark mahogany-colored, glossy foliage and late summer flower display.

The new Ragwort was discovered by the Inventor in August 2001 as a result of a seedling selected from *Ligularia dentata* 'Othello' (not patented) in a garden in Fife, Scotland, United Kingdom. The stated plant is named for the late wife of the Inventor. Asexual reproduction of the Ragwort by tissue culture and division produces stable, true to type plants in successive generations in both of the above mentioned propagation methods, maintaining its distinct and unique color characteristics. Application for Breeder's Right has also been made for *Ligularia dentata* 'Britt-Marie Crawford' in the European Union through the Community Plant Variety Office ("CPVO").

SUMMARY OF THE INVENTION

The cultivar 'Britt-Marie Crawford' has not been observed under all possible environmental conditions. The phenotype may vary somewhat with variations in environment such as temperature, day length and light intensity, without, however, any variance in genotype.

The deep and very dark mahogany-colored, glossy foliage and late summer flower display have been repeatedly observed and determined to be the unique characteristics of 'Britt-Marie Crawford' as distinguished from other Ragwort plants, and in particular from *Ligularia dentata* 'Othello'.

*Ligularia dentata* (A. Gray) is native to eastern China and Japan. There are only a few cultivars known, and *Ligularia stenocephala* 'Little Rocket' (CPVO application number 2002/1174) has patent protection with the Community Plant Variety Office. 'Britt-Marie Crawford' is different from all other *Ligularia* in that it has very dark purple-brown foliage, which is persistent through the season. Other cultivars, such as *Ligularia dentata* 'Desdemona' (not patented) have some purple foliage for a short time in early spring but the purple color disappears as the plant matures. The leaves of 'Britt-Marie Crawford' also have an extremely glossy luster and are more reflective than other forms of Ragwort.

BRIEF DESCRIPTION OF THE PHOTOGRAPHS

The photographs of the new invention demonstrate the overall appearance of the plant including the unique traits. Light source and direction may cause the appearance of variation in the color. The colors are as accurate as reasonably possible with color reproductions.

DETAILED BOTANICAL DESCRIPTION

Figure 1:
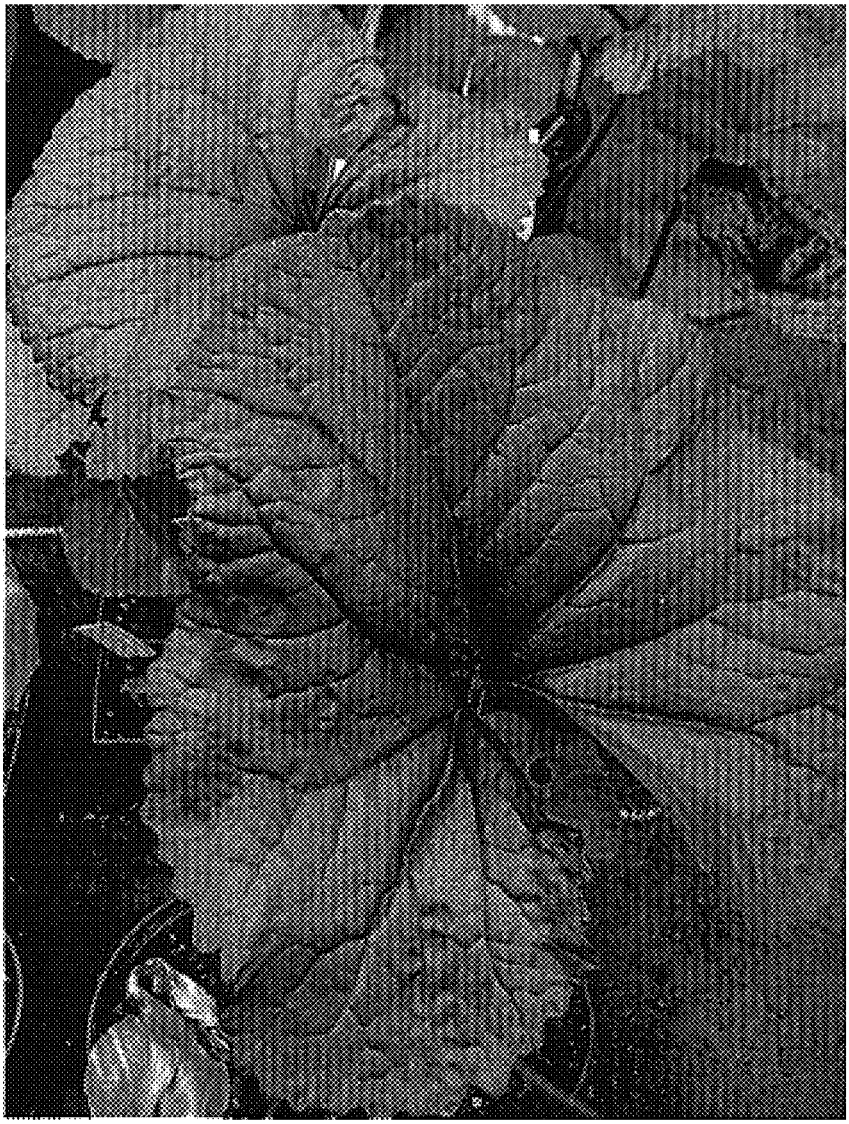
FIG. 1 shows the foliage of the plant.
Figure 2:
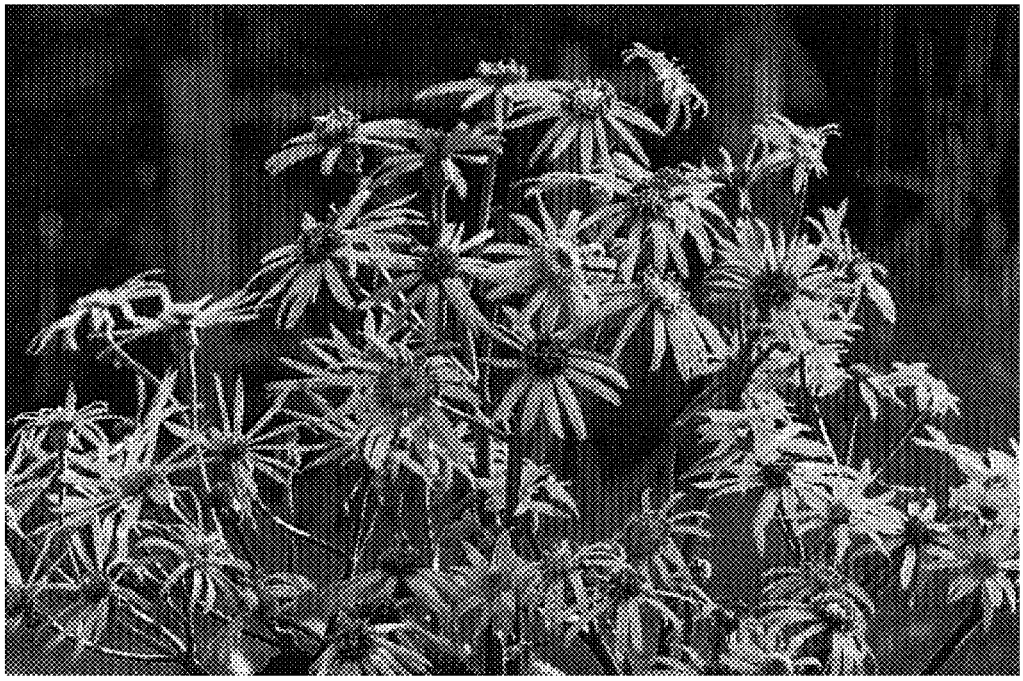
FIG. 2 shows the flowers of the plant in a more mature state of flowering.
Figure 3:
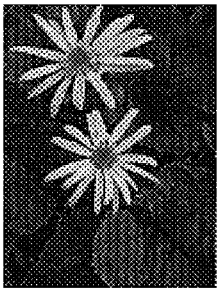
FIG. 3 shows a close-up view of some younger flowers to demonstrate flower color and form.

The following color description is based on color terminology in accordance with the 2001 version of "The Royal Horticultural Society Colour Chart" and is labeled with R.H.S. and the appropriate corresponding reference number and letter, except where common dictionary terms are used. The plant described is a two-year old plant grown in full sun in a garden in Fife, Scotland, United Kingdom in natural outdoor conditions, and under ambient temperatures for the region ranging from lows around 3° C. up to 18° C. during the summer and fall seasons. The plant prefers cool moist soils (41 mm to 66 mm monthly rainfall) and protection from hot afternoon sun, but will recover from wilt if stressed. The plant is not susceptible to any major pests or diseases and is cold tolerant to at least USDA Zone 4.

Botanical classification: *Ligularia dentata* (A. Gray) hybrid.
Parentage: Naturally-occurring whole plant mutation of *Ligularia dentata* 'Othello' (not patented) produced from seedling.
Propagation: Asexual by division and by tissue culture.

Rooting time: Approximately three weeks under greenhouse conditions.

Root description: Thick and fibrous.

Plant habit and form: Clump-forming, herbaceous, perennial, with basal (alternate on stem), long-petioled leaves.

Growth rate: Medium, finishing in a 3-inch pot in approximately 3 months.

Foliage height: 40 to 50 cm.

Foliage spread: 50 to 65 cm.

Leaves: Orbicular-reniform, coarsely dentate margined, 20 to 25 per plant, 16 to 18 cm long, 18 to 22 cm wide, apex rounded, base broadly rounded to cordate, abaxial color RHS 183 C, adaxial color between RHS N187 A and RHS N187 B.

Inflorescence (scapes): Corymbose heads, beginning August and remaining effective for six weeks.

Scape: On mature plants, the scapes can range between 80 to 100 cm tall, 70 to 85 cm wide (as measured diametrically across the plant from the edge of one flower to the edge of a flower on the opposite side) with approximately 70 to 90 flowers per plant.

Ray petals: Approximately 12 to 16 per flower; 22 to 27 mm long, 5 to 7 mm wide; yellow-orange RHS 17 C.

Flower buds at tight petal stage: 1 cm diameter, petals about RHS 17 B.

Disc flowers: Approximately 80 per flower, 4 to 5 mm long, 2 mm wide, RHS 13 B when young, darker than RHS 152 A when mature.

Anthers: 4 to 6 mm long, less than 1 mm wide, darker than RHS 17 A.

Pollen: RHS 17 A.

Seeds: Achenes, approximately 60 to 100 per flower, glabrous, 6 to 8 mm long, 1 to 1.5 mm wide, less than 1 mm thick, dark brown, nearest RHS 200 A.

It is claimed:

1. I claim a new and distinct Ragwort plant named 'Britt-Marie Crawford', as described and illustrated.

* * * * *